United States Patent
Sauer et al.

(10) Patent No.: US 8,992,882 B2
(45) Date of Patent: Mar. 31, 2015

(54) ULTRA-HIGH PURITY ZINC BROMIDES AND QUATERNARY AMMONIUM BROMIDES FOR USE IN ZINC-BROMINE BATTERIES

(75) Inventors: Joe D. Sauer, Baton Rouge, LA (US); George W. Cook, Jr., Baton Rouge, LA (US)

(73) Assignee: Albemarle Corporation, Baton Rouge, LA (US)

( * ) Notice: Subject to any disclaimer, the term of this patent is extended or adjusted under 35 U.S.C. 154(b) by 1247 days.

(21) Appl. No.: 12/528,738

(22) PCT Filed: Feb. 13, 2008

(86) PCT No.: PCT/US2008/053819
§ 371 (c)(1), (2), (4) Date: Aug. 26, 2009

(87) PCT Pub. No.: WO2008/109232
PCT Pub. Date: Sep. 12, 2008

(65) Prior Publication Data
US 2010/0248020 A1  Sep. 30, 2010

Related U.S. Application Data

(60) Provisional application No. 60/892,623, filed on Mar. 2, 2007.

(51) Int. Cl.
*C01B 9/00* (2006.01)
*H01M 6/04* (2006.01)
*C01G 9/04* (2006.01)
*C07C 209/12* (2006.01)
*H01M 12/08* (2006.01)

(52) U.S. Cl.
CPC ............... *C01G 9/04* (2013.01); *C07C 209/12* (2013.01); *H01M 12/085* (2013.01); *C01P 2006/40* (2013.01); *C01P 2006/80* (2013.01)
USPC .......................................... 423/491; 429/188

(58) Field of Classification Search
CPC .............................. C01P 2006/80; C01G 9/04
See application file for complete search history.

(56) References Cited

U.S. PATENT DOCUMENTS 5,599,990 A    2/1997  Miller et al.
6,036,937 A *  3/2000  Dunaway et al. ............. 423/491

FOREIGN PATENT DOCUMENTS

WO    WO 00/29329    5/2000

OTHER PUBLICATIONS

K.J. Cathro, et al; Selection of Quaternary Ammonium Bromides for Use in Zinc/Bromine Cells; J. Power Sources; 1986; vol. 18, pp. 349-370.
Aldrich Handbook of Fine Chemicals and Laboratory Equipment; Aldrich; 2000; p. 1797.

* cited by examiner

*Primary Examiner* — Barbara Gilliam
*Assistant Examiner* — Stephan Essex
(74) *Attorney, Agent, or Firm* — Marcy M. Hoefling; James A. Jubinsky; Nathan C. Dunn

(57) ABSTRACT

Ultra-high purity zinc bromide and quaternary ammonium bromides suitable for use in zinc-bromine batteries, and methods for making same, are provided.

1 Claim, No Drawings

ULTRA-HIGH PURITY ZINC BROMIDES AND QUATERNARY AMMONIUM BROMIDES FOR USE IN ZINC-BROMINE BATTERIES

BACKGROUND

The present invention relates generally to zinc-bromine batteries. More particularly, the present invention relates to improved zinc bromides and quaternary ammonium bromides for use in such batteries, methods of making same, and batteries utilizing same.

A zinc-bromine battery is a type of bipolar, electrochemical flow battery, which is capable of collecting and discharging electric charge. A zinc-bromine battery typically includes a series or stack of voltaic cells, a pump for pumping electrolyte through the cells, terminal electrodes electrically coupled to the stack of cells, and stud terminals electrically coupled to the terminal electrodes and through which electric charge flows into and out of the battery.

The operation of zinc-bromine batteries is described, e.g., is U.S. Pat. No. 5,591,538 and in U.S. Pat. No. 5,650,239. As described therein, the battery cells are made up of a series of alternating electrodes and separators. The electrodes are said to be "bipolar" because an anodic reaction takes place on one side of the electrode and a cathodic reaction takes place on its opposite side. Therefore, each cell can be considered as having an anodic half-cell and a cathodic half-cell. An ion permeable separator separates the anodic half-cell from the cathodic half-cell. Electrolyte is pumped through each half-cell, i.e., an anolyte through the anodic half-cell, and a catholyte through the anodic half-cell.

The electrolyte in zinc-bromine batteries is an aqueous solution of zinc bromide and quaternary ammonium salts, for example, methylethylpyrrolidinium bromide, with optional supporting salts, such as $NH_4Cl$, and it is circulated through the individual cells from external reservoirs. It should be understood that the battery may be in several states including a discharged state and a charged state.

In the discharged state, the anolyte is substantially chemically identical to the catholyte. During the process of collecting a charge, the following chemical reactions take place:

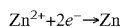
$$Zn^{2+}+2e^-\rightarrow Zn$$

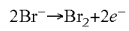
$$2Br^-\rightarrow Br_2+2e^-$$

Zinc is plated on the anode, and bromine is produced at the cathode. The bromine is immediately complexed by the quaternary ammonium ions in the electrolyte to form a dense second phase which is subsequently removed from the battery stack with the flowing electrolyte. Further, and when the battery is charged, zinc in stored on one side of each electrode and the complex bromine is stored in the catholyte reservoir.

During the electrical discharge process, the following chemical reactions takes place:

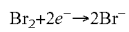
$$Br_2+2e^-\rightarrow 2Br^-$$

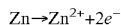
$$Zn\rightarrow Zn^{2+}+2e^-$$

In this reaction, zinc is oxidized, and the released electrons pass through the electrode where they combine with molecular bromine to form bromide ions. Further, the positively charged zinc ions travel through the separator and remain in solution, and at the same time, bromide ions pass through the separator in the opposite direction and remain in solution.

Zinc-bromine batteries have several advantages over other types of batteries. In particular, one such advantage is the relatively high energy storage capacity of a zinc-bromine battery. Even though zinc-bromine batteries are in many ways superior to other types of batteries, current commercial technologies for zinc-bromine batteries are not completely satisfactory. For example, specifications for the entire electrolyte system are stringent and require low part per million ("ppm") levels of most of the transition metals; this being a quality issue to maintain recycle performance in the battery assembly after many charge/discharge cycles. The quaternary ammonium salt component typically must be fluid, capable of containing elemental bromine, and stable to the various operating conditions within electrochemical flow battery.

Commonly utilized classes of quaternary ammonium salts are dialkylpyrrolidinium halides, dialkylmorpholinium halides, and dialkylpiperidinium halides, including, e.g., methylethylpyrrolidinium bromide "MEP" and methylethylmorpholinium bromide "MEM". However, all of these salts, unless used in suitable combinations with other components, allow formation of crystallite structure of the salts and the zinc bromides, which would ultimately short out the flow batteries if costly, time-consuming maintenance procedures are not performed.

Therefore, there is a need for zinc bromides that meet the purity standards for zinc-bromine batteries, a need for commercially suitable quaternary ammonium salts, and a need for zinc-bromine batteries that utilize the zinc bromides and quaternary ammonium salts.

THE INVENTION

This invention provides ultra-high purity zinc bromides and commercially suitable quaternary ammonium bromides, methods for making same, and methods for using same in zinc-bromine batteries, and thus fulfills the above-described needs.

This invention provides methods comprising combining bromine with at least about 1 percent to about 10 percent molar excess zinc metal and producing zinc bromide. About 5 percent to about 6 percent molar excess zinc metal can be combined with bromine. These methods according to this invention produce ultra-high purity zinc bromides.

This invention also provides methods comprising combining an amine with a molar excess of n-propyl bromide and producing quaternary ammonium bromide.

This invention also provides zinc-bromine batteries that uses zinc bromide produced by a method comprising combining bromine with at least about 1 percent molar excess zinc metal to about 10 percent molar excess zinc metal, and uses quaternary ammonium bromide produced by a method comprising combining amine with a molar excess of n-propyl bromide.

This invention is described in connection with specific embodiments. It is understood that this invention is not limited to any one of these specific embodiments.

Ultra-High Purity Zinc Bromide

We have discovered that ultra-high purity zinc bromide can be produced by reacting an excess of zinc metal with a limited amount of elemental bromine. Such a reaction leaves a heel of zinc metal that also contains the metal impurities introduced in the feedstock zinc with the soluble zinc bromide being isolable in highly pure form. As an additional benefit, this process also improves the quality of the quaternary ammonium bromide present in the system in that any impurities present therein stay in the unreacted zinc metal.

Processes of this invention enable the use of normal grades of zinc metal, normal purities of commercial bromine, and fairly low-quality grades of quaternary ammonium bromides and still accomplishes the production of high purity, high quality electrolytic solutions. The excess zinc heel can be recovered and utilized in suitable commercial operations.

Quaternary Ammonium Bromides

The quaternary ammonium bromides prepared according to this invention can be prepared by combining alkyldimethylamine "ADMA" or dialkylmethylamine "DAMA", with a molar excess of n-propyl bromide "NPB". In methods of this invention, the NPB acts essentially as a solvent; and excess NPB can be removed. Temperatures can range from about boiling point of NPB to about 150° C.; pressures can range from about atmospheric to about 200 psi; and conversions to essentially quantitative yields of the desired quaternary ammonium bromide are relatively rapid, e.g., about 12 hours at atmospheric pressure and about 4 hours at pressures up to about 200 psi. Any suitable tertiary amine or tertiary amine blend, such as ADMA or DAMA, would be useful in methods of this invention, including, for example, ADMA 8 and DAMA 810, as produced by Albemarle Corporation.

Use of NPB as the alkylating agent for suitable parent amines, e.g., aklylpyrrolidine, alkylmorpholine, and alkylpiperdine, generates quaternary ammonium bromides that have improved resistance to crystallite formation, as compared to current commercial quaternary ammonium bromides. The propyl group would fit more poorly in a crystal lattice than the methyl- or ethyl-analogues of current commercial quaternary ammonium bromides.

Zinc-Bromine Batteries

Zinc-bromine batteries according to this invention comprise ultra-high purity zinc bromide and quaternary ammonium bromide as described herein, and produced according to methods described herein. An advantage to zinc-bromine batteries of this invention is that elemental bromine can be added as the battery cycles, leading to production within the battery of corresponding ammonium trihalide complexes, for example, tetra-alkyl aliphatic quaternaryammonium halides, di-alkyl pyrrolidinium halides, di-alkyl piperidinium halides, and di-alkyl morpholinium halides, which are useful as phase transfer agents.

The electrolyte in zinc-bromine batteries according to this invention can be an aqueous solution comprising ultra-high purity zinc bromide and quaternary ammonium bromide as described herein, and produced according to methods described herein. For example, ultra-high purity zinc bromide and methylethylpyrrolidinium bromide, with optional supporting salts, such as $NH_4Br$, can be circulated through the individual cells from external reservoirs. It should be understood that the battery may be in several states including a discharged state and a charged state.

EXAMPLES

Ultra-High Purity Zinc Bromide

Comparative Example

Baseline 1.40 mole zinc metal powder was slurried in 100 mL distilled and deionized "DDI" water and 1.40 mole elemental bromine was added, in a drop-wise basis over several hours. After 12 hours, the resulting solution of zinc bromide was a yellow, slightly viscous liquid.

The baseline run generated zinc bromide solutions with trace levels of transition metals ranging from 1 ppm (Ag); >500 ppm (Pb); 8 ppm (Cd); 3 ppm (Cu); 4 ppm (Se); ~1 ppm (Fe).

Example 1

1.49 mole zinc metal powder was slurried in 100 mL DDI water and 1.40 mole elemental bromine was added, in a drop-wise basis over several hours. After 12 hours, the resulting slurry was filtered (to remove the ~6% excess zinc metal) and the solution of zinc bromide was a very pale yellow, slightly viscous liquid.

The Example 1 run generated zinc bromide solutions with trace levels of transition metals as indicated: <1 ppm (Ag); <1 ppm (Pb); <1 ppm (Cd); <1 ppm (Cu); <1 ppm (Se); <1 ppm (Fe).

Example 2

1.49 mole zinc metal powder was slurried in 100 mL DDI water and 1.40 mole elemental bromine was added, in a drop-wise basis over several hours. After 6 hours, the resulting slurry was filtered (to remove the ~6% excess zinc metal) and the solution of zinc bromide was, as in example 1, a very pale yellow, slightly viscous liquid.

The Example 2 run generated zinc bromide solutions with trace levels of transition metals as indicated: <1 ppm (Ag); <1 ppm (Pb); <1 ppm (Cd); <1 ppm (Cu); <1 ppm (Se); <1 ppm (Fe).

Example 3

1.12 mole zinc metal powder was slurried in 75 mL DDI water containing 0.36 mole of methyl-ethyl-pyrrolidinium [MEP] bromide. To this mixture, 1.06 mole elemental bromine was added, in a drop-wise basis over several hours. After 5 hours, the resulting slurry was filtered (to remove the ~6% excess zinc metal) and the solution of zinc bromide was a colorless, slightly viscous liquid.

The Example 3 run (with only MEP present as the quaternary agent) generated zinc bromide solutions with trace levels of transition metals as indicated: <1 ppm (Ag); <1 ppm (Pb); <1 ppm (Cd); <1 ppm (Cu); <1 ppm (Se); <1 ppm (Fe).

Example 4

1.12 mole zinc metal powder was slurried in 75 mL DDI water containing 0.36 mole of methyl-ethyl-morpholinium [MEM] bromide. To this mixture, 1.06 mole elemental bromine was added, in a drop-wise basis over several hours. After 4 hours, the resulting slurry was filtered (to remove the ~6% excess zinc metal) and the solution of zinc bromide was a colorless, slightly viscous liquid.

The Example 4 run (with only MEM present) generated zinc bromide solutions with trace levels of transition metals as indicated: <1 ppm (Ag); <1 ppm (Pb); <1 ppm (Cd); <1 ppm (Cu); <1 ppm (Se); <1 ppm (Fe).

Example 5

1.12 mole zinc metal powder was slurried in 75 mL DDI water containing 0.18 mole of methyl-ethyl-pyrrolidinium bromide and 0.18 mole of methyl-ethyl-morpholinium bromide. To this mixture, 1.06 mole elemental bromine was added, in a drop-wise basis over several hours. After 3.5 hours, the resulting slurry was filtered (to remove the ~6% excess zinc metal) and the solution of zinc bromide was a colorless, slightly viscous liquid.

The Example 5 run (with both MEP and MEM present) generated zinc bromide solutions with trace levels of transition metals as indicated: <1 ppm (Ag); <1 ppm (Pb); <1 ppm (Cd); <1 ppm (Cu); <1 ppm (Se); <1 ppm (Fe).

Analysis of the zinc heel in Examples 1 through 5 accounted for the missing transition metals with typical values being: 44 ppm (Ag); 1600 ppm (Pb); 220 ppm (Cd); 100 ppm (Cu); <6 ppm (Se); 13 ppm (Fe). The color bodies present in the crude quaternary ammonium bromides are also eliminated (from dark brown in raw quat to colorless in the finished electrolyte solutions).

It is to be understood that the reactants and components referred to by chemical name or formula anywhere in the specification or claims hereof, whether referred to in the singular or plural, are identified as they exist prior to being combined with or coming into contact with another substance referred to by chemical name or chemical type (e.g., another reactant, a solvent, or etc.). It matters not what chemical changes, transformations and/or reactions, if any, take place in the resulting combination or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a combination to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, combined, blended or mixed with one or more other substances, components and/or ingredients in accordance with the present disclosure. Whatever transformations, if any, which occur in situ as a reaction is conducted is what the claim is intended to cover. Thus the fact that a substance, component or ingredient may have lost its original identity through a chemical reaction or transformation during the course of contacting, combining, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof. As will be familiar to those skilled in the art, the terms "combined", "combining", and the like as used herein mean that the components that are "combined" or that one is "combining" are put into a container with each other. Likewise a "combination" of components means the components having been put together in a container.

While the present invention has been described in terms of one or more preferred embodiments, it is to be understood that other modifications may be made without departing from the scope of the invention, which is set forth in the claims below.

We claim:

1. A method consisting essentially of combining elemental bromine with at least about 1 percent molar excess feedstock zinc metal to about 10 percent molar excess feedstock zinc metal, which feedstock zinc metal contains transition metal impurities comprising one or more of greater than 500 ppm Pb, at least 3 ppm Cu, and at least 1 ppm Fe, and producing an isolable zinc bromide composition comprising less than 1 ppm Pb, less than 1 ppm Cu, and less than 1 ppm Fe, which method leaves a heel of zinc metal that contains the transition metal impurities that are missing from the produced isolable zinc bromide composition.

* * * * *